(12) United States Patent
Delaney, Jr. et al.

(10) Patent No.: US 11,224,666 B2
(45) Date of Patent: Jan. 18, 2022

(54) GADOLINIUM CONTRAST AGENTS, SCAVENGING METHODS, AND SCAVENGING SYSTEM

(71) Applicant: Boston Scientific Scimed, Inc., Maple Grove, MN (US)

(72) Inventors: Joseph Thomas Delaney, Jr., Minneapolis, MN (US); Douglas Dean Pagoria, Evergreen, CO (US); Douglas Pennington, Stillwater, MN (US); Paul Sorajja, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/276,169

(22) Filed: Feb. 14, 2019

(65) Prior Publication Data

US 2019/0247523 A1     Aug. 15, 2019

Related U.S. Application Data

(60) Provisional application No. 62/630,623, filed on Feb. 14, 2018.

(51) Int. Cl.
*A61K 49/10* (2006.01)
*A61K 47/54* (2017.01)

(52) U.S. Cl.
CPC ............ *A61K 49/10* (2013.01); *A61K 47/555* (2017.08); *A61K 49/103* (2013.01)

(58) Field of Classification Search
CPC .. A61K 49/103; A61K 49/105; A61K 49/106; A61K 49/108; A61K 49/10; A61K 47/555; A61F 2/01
See application file for complete search history.

(56) References Cited

U.S. PATENT DOCUMENTS

| | | | |
|---|---|---|---|
| 8,545,813 B2 | 10/2013 | Song et al. | |
| 2008/0181847 A1* | 7/2008 | Robillard | A61K 51/0491 424/1.11 |
| 2016/0346409 A1* | 12/2016 | Valliant | A61K 49/221 |

FOREIGN PATENT DOCUMENTS

| | | |
|---|---|---|
| WO | 2011017690 | 2/2011 |

OTHER PUBLICATIONS

Grogna et al., Polym. Chem., 2011, 2, 2316-27. (Year: 2011).*
Grogna, Mathurin et al., "Stealth macromolecular platforms for the design of MRI blood pool contrast agents," Polym. Chem. 2011, 2, 2316-27 (12 pages).
Hapuarachchige, Sudath et al., "Click Chemistry in the Development of Contrast Agents for Magnetic Resonance Imaging," Topics In Magnetics Resonance Imaging, vol. 25, No. 5, Oct. 1, 2016 pp. 205-213 (20 pages).
International Search Report and Written Opinion for PCT Application No. PCT/US2018/018005 dated Oct. 24, 2019 (12 pages).
Kobayashi, Hisataka et al., "Activated Clearance of a Biotinylated Macromolecular MRI Contrast Agent from the Blood Pool using an Avidin Chase," Bioconjugate Chemistry, vol. 14, No. 5, Sep. 1, 2003 pp. 1044-1047 (4 pages).
Yantasee, W. et al., "Novel sorbents for removal of gadolinium-based contrast agents in sorbent dialysis and hemoperfustion: preventive approaches to nephrogenic systemic fibrosis," Nanomedicine: Nanotechnology, Biology and Medicine, Elsevier, NL, vol. 6, No. 1, Feb. 1, 2010 pp. 1-8 (8 pages).
Liu, Hui et al., "Ultrafast Click Chemistry with Fluorosydnones," Agnew. Chem. Int. Ed. Engl. 2016, 55(39), 12073-7 (5 pages).
Pokorski, Jonathan K. et al., "Functional Virus-Based Polymer-Protein Nanoparticles by Atom Transfer Radical Polymerization," J Am Chem Soc, 2011. 133(24): 9242-5 (11 pages).
Ramil, Carlo P. et al., "Bioorthogonal Chemistry: Strategies and Recent Developments," Chem. Commun. 2013, 49(94), 11007-22 (16 pages).
Rogosnitzky, Moshe et al., "Gadolinium-based Contrast Agent Toxicity: a Review of Known and Proposed Mechanisms," Biometals (2016) 29:365-376 (12 pages).
Santra, Santimukul et al., "Aliphatic Hyperbranched Polyester: A New Building Block in the Construction of Multifunctional Nanoparticles and Nanocomposites," Langmuir 2010, 26(18), 5364-73 (10 pages).
Sukerkar, Preeti A. et al., "Synthesis and Biological Evaluation of Water-soluble Progesterone-Conjugated Probes for Magnetic Resonance Imaging of Hormone Related Cancers," Bioconjug Chem, 2011. 22(11): 2304-16 (26 pages).
Tan, Mingqian et al., "Peptide-Targeted Nanoglobular Gd-DOTA Monoamide Conjugates for Magnetic Resonance Cancer Molecular Imaging," Biomacromolecules, 2010. 11(3): 754-61 (8 pages).
Toppino, Antonio et al., "A carborane-Derivative "Click" Reaction under Heterogeneous Conditions for the Synthesis of a Promising Lipophilic MRI/GdBNCT Agent," Chemistry, 2013. 19(2): 721-8 (8 pages).
Vanasschen, Christian et al., "Gadolinium DOTA Chelates Featuring Alkyne Groups Directly Grafted on the Tetraaza Macrocyclic Ring: Synthesis, Relaxation Properties, "Click" Reaction, and High-Relaxivity Micelles," Inorg Chem, 2011. 50(18): 8946-58 (13 pages).

(Continued)

*Primary Examiner* — Michael G. Hartley
*Assistant Examiner* — Leah H Schlientz
(74) *Attorney, Agent, or Firm* — Pauly, DeVries Smith & Deffner LLC

(57) ABSTRACT

A functional gadolinium contrast agent comprising a gadolinium cation and a ligand secured to the gadolinium cation is disclosed, the ligand comprising a reactive group capable of bonding to a capture substrate. A method of removing gadolinium contrast agents from a patient is disclosed, the method comprising providing a gadolinium contrast agent containing a reactive group; providing a capture substrate for insertion into a patient's bloodstream; administering the gadolinium contrast agent to the patient; conducting a magnetic resonance imaging procedure; and sequestering the gadolinium contrast agent on the capture substrate. A system for removing gadolinium contrast agents is also disclosed.

6 Claims, 6 Drawing Sheets

(56) References Cited

OTHER PUBLICATIONS

Verwilst, Peter et al., "A Modular Approach towards the Synthesis of Target-Specific MRI Contrast Agents," European Journal of Inorganic Chemistry, 2011. 2011(24): 3577-85 (9 pages).
International Preliminary Report on Patentability for PCT Application No. PCT/US2018/018005 dated Aug. 27, 2020 (9 pages).
"Response to Communication Pursuant to Rules 161(1) and 162 EPC," for European Patent Application No. 19707637.5 filed Apr. 1, 2021 (10 pages).

* cited by examiner

US 11,224,666 B2

GADOLINIUM CONTRAST AGENTS, SCAVENGING METHODS, AND SCAVENGING SYSTEM

This application claims the benefit of U.S. Provisional Application No. 62/630,623, filed Feb. 14, 2018, the content of which is herein incorporated by reference in its entirety.

FIELD OF THE INVENTION

The present technology generally relates to gadolinium contrast agents, including gadolinium contrast agents modified to be scavenged from a patient, as well as methods and systems for scavenging gadolinium contrast agents from a patient.

BACKGROUND

Contrast agents are commonly used in magnetic resonance imaging (MRI) to enhance and improve the quality of the MRI images. Gadolinium contrast agents are formed of a gadolinium chelate that includes a $Gd^{3+}$ cation plus a ligand that typically contains three or four amine groups securing a gadolinium cation. The ligand also often includes a plurality of acid or amide groups. The ligand isolates the gadolinium cation, preventing it from being rapidly absorbed by cells, while also influencing and improving imaging contrast properties.

Gadolinium contrast agents and their byproducts are often excreted unchanged by glomerular filtration. However, studies have shown that gadolinium can accumulate in tissues, such as brain tissue, bone tissue, and kidney tissue. This accumulation in a patient's tissues can be problematic, especially for patients with reduced renal function. Symptoms of gadolinium accumulation include central pain, peripheral pain, headaches, bone pain, skin thickening, clouded mentation, etc.

Therefore, a need exists for a way to effectively remove gadolinium contrast agents from a patient's bloodstream after undergoing MRI procedures.

SUMMARY

Embodiments include functionalized gadolinium contrast agents, system for removing gadolinium contrast agent from a patient, and methods for removing gadolinium contrast agent from a patient In a first aspect, a functionalized gadolinium contrast agent has a gadolinium cation; and a ligand secured to the gadolinium cation, the ligand comprising a reactive group capable of bonding to a capture molecule on a capture substrate.

In a second aspect, in addition or in place of other aspects herein, the ligand secured to the gadolinium cation comprises a plurality of amine groups.

In a third aspect, in addition or in place of other aspects herein, the ligand secured to the the gadolinium cation comprises a plurality of acid groups.

In a fourth aspect, in addition or in place of other aspects herein, the reactive group on the ligand comprises an azide group.

In a fifth aspect, in addition or in place of other aspects herein, the reactive group on the ligand comprises an azide, alkyne, tetrazine, fluorosydnones, or combinations thereof.

In a sixth aspect, in addition or in place of other aspects herein, the capture substrate comprises a strained alkyne.

In a seventh aspect, in addition or in place of other aspects herein, the strained alkyne of the capture substrate is selected from the group OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

In an eighth aspect, in addition or in place of other aspects herein, the functionalized gadolinium contrast agent forms a covalent bond with the capture molecule on the capture substrate when brought in contact with each other.

In a ninth aspect, in addition or in place of other aspects herein, the functionalized gadolinium contrast agent and the capture molecule form a tri-azole ring upon reacting.

In a tenth aspect, in addition or in place of other aspects herein, a system for removing gadolinium contrast agent from a patient includes a gadolinium contrast agent comprising a gadolinium cation secured to a ligand comprising a reactive group capable of bonding to a capture molecule on a capture substrate; and a capture substrate containing a capture molecule capably of spontaneously forming a bond with the reactive group on the gadolinium contrast agent.

In an eleventh aspect, in addition or in place of other aspects herein, the reactive group on the ligand comprises an azide group.

In a twelfth aspect, in addition or in place of other aspects herein, the gadolinium cation secured to the ligand comprises an azide reactive group; the capture substrate comprises a polymer containing a strained alkyne; the strained alkyne selected from the group OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne), and mixtures thereof.

In a thirteenth aspect, in addition or in place of other aspects herein, the capture substrate comprises a textile, membrane, foam, gel, web, or combination of substrates.

In a fourteenth aspect, in addition or in place of other aspects herein, a method of removing gadolinium contrast agents from a patient includes providing a gadolinium contrast agent comprising a reactive group; providing a removable capture substrate containing a capture molecule that spontaneously bonds to the reactive group of the gadolinium contrast agent; administering the gadolinium contrast agent to a patient; conducting a magnetic resonance imaging procedure; and sequestering the gadolinium contrast agent on the removable capture substrate.

In a fifteenth aspect, in addition or in place of other aspects herein, the removable capture substrate is positioned in a blood vessel upstream of the kidney of the patient during sequestration of the gadolinium contrast agent.

In a sixteenth aspect, in addition or in place of other aspects herein, the gadolinium contrast agent comprises a plurality of amine groups.

In a seventeenth aspect, in addition or in place of other aspects herein, gadolinium contrast agent comprises an azide group.

In an eighteenth aspect, in addition or in place of other aspects herein, the gadolinium contrast agent comprises an azide, alkyne, tetrazine, fluorosydnones, or combinations thereof.

In a nineteenth aspect, in addition or in place of other aspects herein, the capture substrate comprises group OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

In a twentieth aspect, in addition or in place of other aspects herein, the capture substrate comprises a textile, foam, or web.

The present disclosure is also directed to a method of removing gadolinium contrast agents from a patient, the method comprising providing a gadolinium contrast agent comprising a reactive group; providing a removable capture substrate containing a capture molecule that spontaneously bonds to the reactive group of the gadolinium contrast agent; administering the gadolinium contrast agent to a patient; conducting a magnetic resonance imaging procedure; and sequestering the gadolinium contrast agent on the removable capture substrate while allowing blood to flow through.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

BRIEF DESCRIPTION OF THE DRAWINGS

The present subject matter may be more completely understood and appreciated in consideration of the following detailed description of various embodiments in connection with the accompanying drawings.

While embodiments herein are susceptible to various modifications and alternative forms, specifics thereof have been shown by way of example and drawings and will be described in detail. It should be understood, however, that the scope herein is not limited to the particular examples described. On the contrary, the intention is to cover modifications, equivalents, and alternatives falling within the spirit and scope herein.

DETAILED DESCRIPTION

Gadolinium containing MRI contrast agents are among the most commonly used for enhancement of vessels in MRI angiography. For large vessels such as the aorta and its branches, the gadolinium dose can be as low as 0.1 mmol per kilogram of body mass. Higher concentrations are often used for finer vasculature. Although gadolinium contrast agents and their byproducts are mostly excreted unchanged by glomerular filtration, studies have shown gadolinium accumulates in tissues, such as brain, bone, and kidneys. The ionic radius of $Gd^{+3}$ is very close to that of the calcium cation $Ca^{+2}$. Due to the similar size and charge, free gadolinium can be a competitive inhibitor of physiologic processes that depend on $Ca^{+2}$ influx, including voltage-gated calcium channels and the activity of some enzymes. Therefore, gadolinium-based MRI contrast agents typically use some sort of ligand to chelate the free ion and reduce its toxicity. Still, a need exists for assisted removal of gadolinium, in particular gadolinium chelates, from the bloodstream. This need is especially important on patients with diminished kidney function.

The present disclosure is directed to gadolinium contrast agents that have been modified to provide a functional group that can spontaneously covalently bond to a capture molecule secured to a removable substrate and then removed from a patient. The bond between the gadolinium contrast agent and the capture molecule allows for subsequent removal of the gadolinium contrast agent by removal of the substrate containing the capture molecules. More specifically, water-soluble gadolinium-based contrast agents are modified with functional groups so that the contrast agent can selectively, rapidly react with a biorthogonal counterpart capture molecule secured to a substrate, and this substrate can then be removed from the patient (if the substrate is positioned within the patient); or alternatively an external capture element can be used that contains the capture molecule secured to a substrate. As such, the gadolinium contrast agents and reactive substrate utilize "click chemistry" to selectively and effectively remove the gadolinium contrast agents from a patient's bloodstream.

Figure 1:
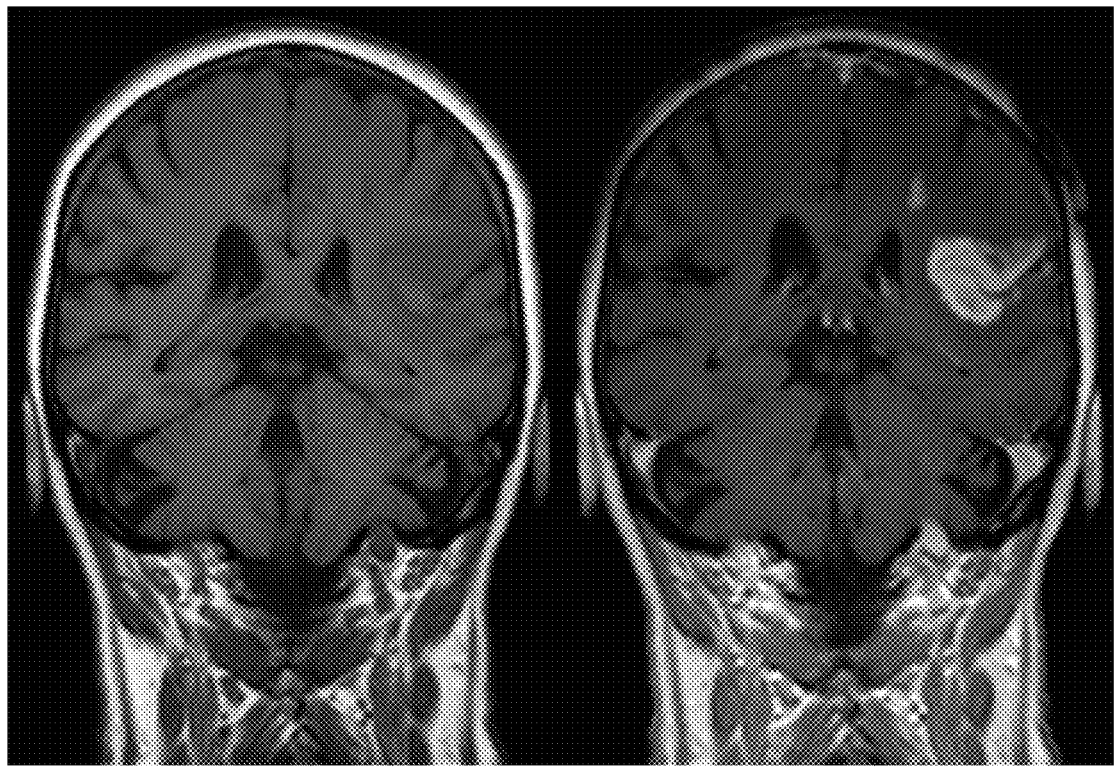
FIG. 1 shows two magnetic resonance images of a human head, with the left image taken without a gadolinium contrast agent and the right image taken with a gadolinium contrast agent.

Referring now to the drawings, FIG. 1 shows two magnetic resonance images of a human head, with the left image taken without a gadolinium contrast agent and the right image taken with a gadolinium contrast agent. As can be seen in FIG. 1, the gadolinium contrast agent provides improved imaging, revealing an area of increased blood volume (and thus a potential aneurism) on the right side of the patient's brain. Thus, the benefits of use of a gadolinium contrast agent are clearly shown in FIG. 1

As detailed further below, the gadolinium contrast agent is typically a linear or macrocyclic structure. Linear agents have an elongated organic molecular ligand that wraps around the gadolinium ion. Macrocyclic agents form a cage-like ligand structure with the ion trapped in a preformed central cavity. Both linear and macrocyclic agents can either be ionic or non-ionic. In the macrocyclic structure, the gadolinium ion is retained in a cavity of the ligand. Both linear and macrocyclic gadolinium contrast agents can be produced or modified for improved removal from a patient using click chemistry.

The gadolinium contrast agent, whether linear or macrocyclic, can be modified to add a reactive group capable of bonding to a capture substrate. One example modification is to add an azide group to the gadolinium ligand. An azide group can be particularly useful because it is small, metabolically stable, and does not naturally exist in cells. Thus, azide groups generally have no competing biological side reactions and thus are particularly selective when binding to an appropriately-selected biorthogonal pair, such as a strained alkyne secured to a substrate.

Figure 2A:
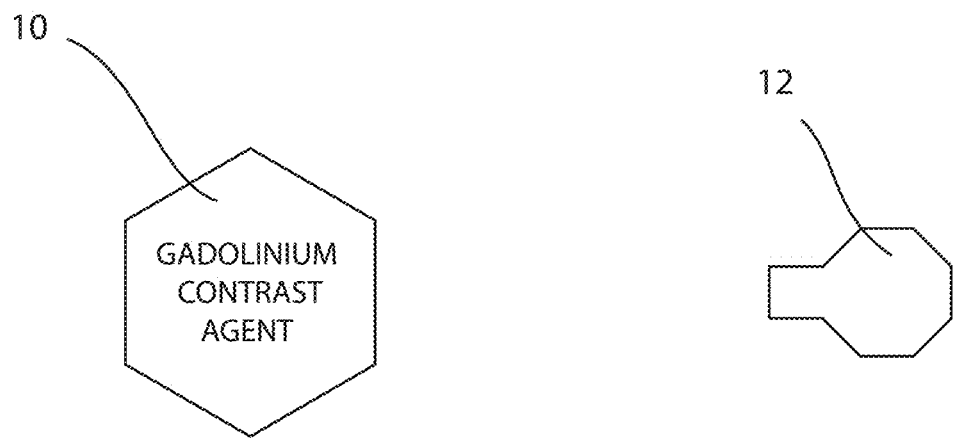
FIG. 2A is a schematic diagram of a gadolinium contrast agent prior to addition of a reactive group.
Figure 2B:
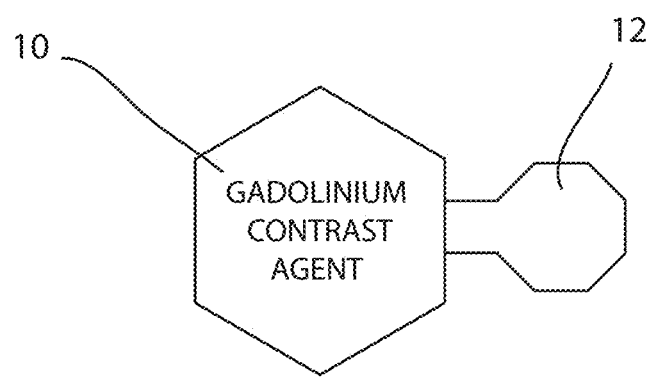
FIG. 2B is a schematic diagram of a gadolinium contrast agent after addition of a reactive group.

FIG. 2A is a schematic diagram of a gadolinium contrast agent 10 prior to addition of a reactive group 12, and FIG. 2B is a schematic of a gadolinium contrast agent 10 after addition of the reactive group 12. FIG. 2B shows the gadolinium contrast agent 10 with the reactive group 12, such as an azide, attached. An example of a specific linear gadolinium contrast agent to which an azide is attached is reproduced below, showing gadofosvaset with an azide group added to the aromatic ring.

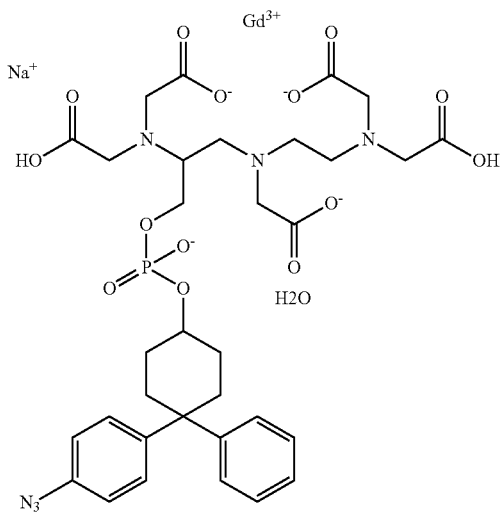

The gadolinium contrast agent can be initially formed, and then modified to include the reactive group 12, or the reactive group 12 can simultaneously be added during synthesis of the overall gadolinium contrast agent. Thus, the inclusion of one or more reactive groups 12 can be done at various stages of creation of the gadolinium contrast agent.

Figure 3:
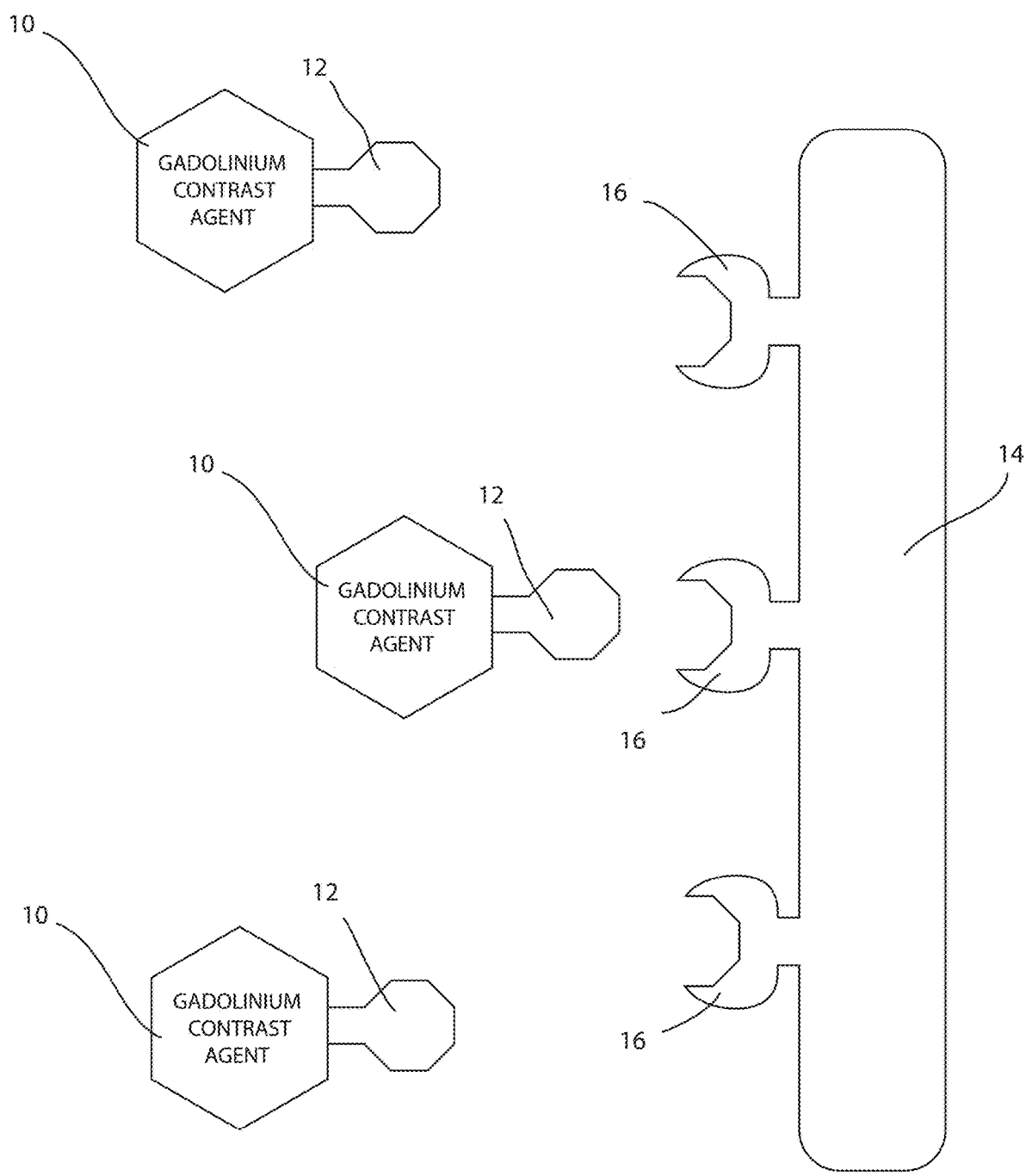
FIG. 3 is a schematic diagram of gadolinium contrast agents to which reactive groups have been added, shown with a reactive substrate.

Referring now to FIG. 3, a schematic representation is shown of multiple gadolinium contrast agent molecules 10 from FIG. 2 with reactive groups 12 (such azides), along with a capture substrate 14. The capture substrate 14 includes capture molecules 16, such as strained alkynes, capable of a spontaneous, irreversible reaction with reactive groups 12. The capture molecule 16 can include, for example, OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

In FIG. 3 the capture molecules 16 are shown secured to the capture substrate 14, but without any of the contrast agent molecules 10 yet reacted with the capture molecules 16.

Figure 4:
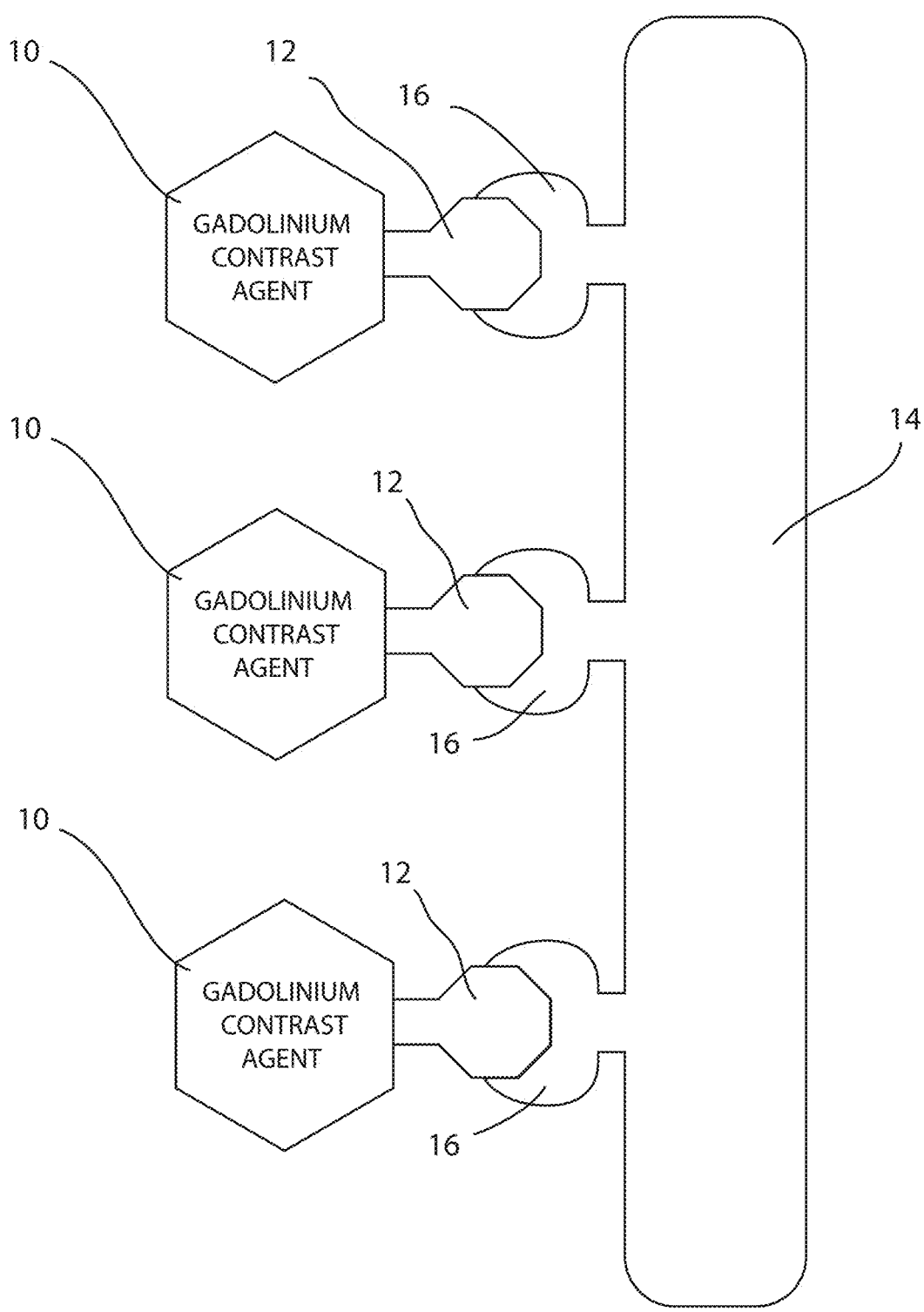
FIG. 4 is schematic diagram of gadolinium contrast agents to which reactive groups have been added, showing the gadolinium contrast agents sequestered on a reactive substrate.

FIG. 4 is a schematic of molecules of gadolinium contrast agent 10 to which reactive groups 12 have been added, showing the gadolinium contrast agents 10 sequestered on the capture substrate 14 by way of the reactive groups 12 of the contrast agent 10 having reacted with the capture molecules 16 of the capture substrate 14. The capture substrate 14 can be, for example, a polymeric film, gel, web, fabric, foam, mesh or other material to which the capture molecules 16 have been secured, or a combination of materials. After the capture molecules 16 bind to gadolinium contrast agents 10, the entire substrate 14 and accompanying secured gadolinium contrast agents 10 can be removed from a patent. For example, in some implementations the substrate 14 is placed within a blood vessel in a patient, such as blood vessels upstream of the kidney (for example, in the left or right renal artery, or the interior vena cava). Alternatively, the substrate 14 is positioned outside of the patient's body within a housing connected by intravenous catheters to the patient's bloodstream.

Synthesis of components of an example linear or open chain gadolinium contrast agent is shown below (without the gadolinium cation present):

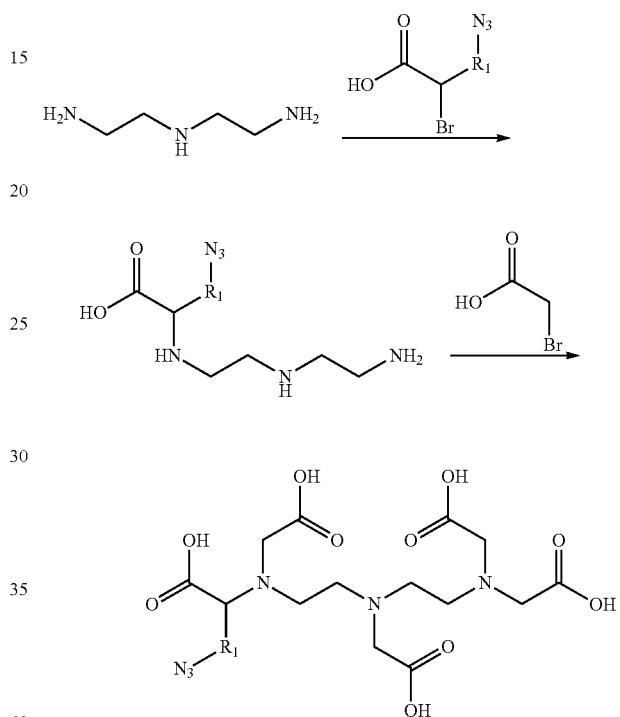

Synthesis of components of an example macrocyclic gadolinium contrast agent is shown below (without the gadolinium cation present):

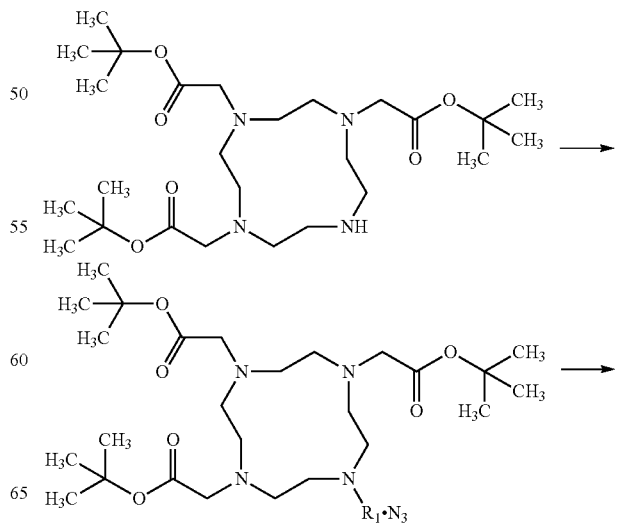

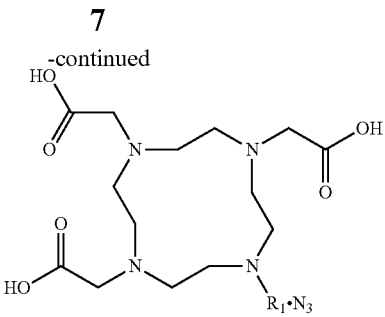

An alternative synthesis for the macrocyclic gadolinium contrast agent is shown below, including addition of a reactive azide group:

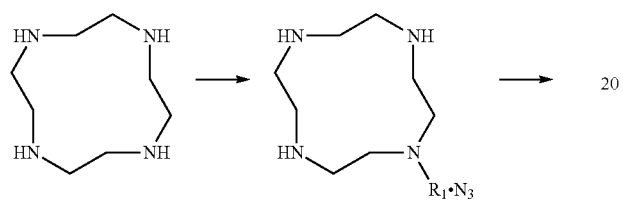

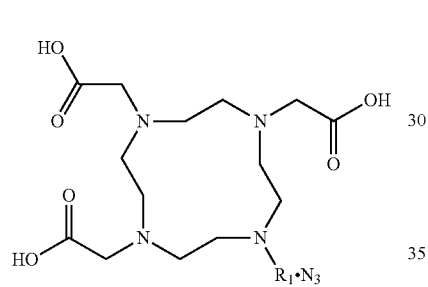

The gadolinium contrast agents, whether linear or macrocyclic, are modified to add a reactive group capable of bonding to a capture substrate. One example modification is to add an azide group to the gadolinium ligand. More generally, the reactive group of the ligand can be, for example, an azide, alkyne, tetrazine, fluorosydnones, or combinations thereof. The azide group is particularly appropriate because it is small, metabolically stable, and does not naturally exist in cells. Thus, it has no competing biological side reactions. The alkyne is not as small, but it still has the stability and orthogonality useful for selective removal of gadolinium contrast agents.

Desired properties for the ligand comprising the reactive group and the related capture substrate include strong selectivity, generally biological inertness, generally biological and chemical inertness, favorable kinetics, and reaction biocompatibility. With regard to selectivity, it is desirable that the reaction be selective between functional groups to avoid side reactions with biological compounds. With regard to biological inertness, desirably the reactive group on the contrast ligand should not possess reactivity capable of disrupting the native chemical functionality of the patient. Regarding chemical inertness, the covalent link between the reactive group on the ligand and the capture molecule on the capture substrate should be strong and inert to biological reactions.

An example of a linear gadolinium contrast agent without a reactive group is shown below (and is the same contrast agent shown above, also referred to as "gadofosvaset", prior to addition of an azide group):

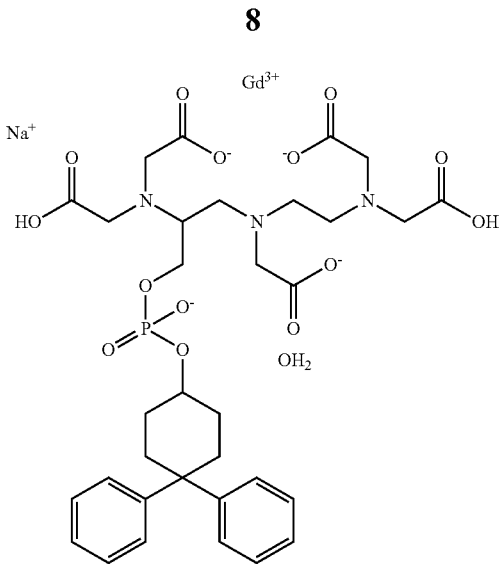

This same contrast agent, after adding an azide group is shown below:

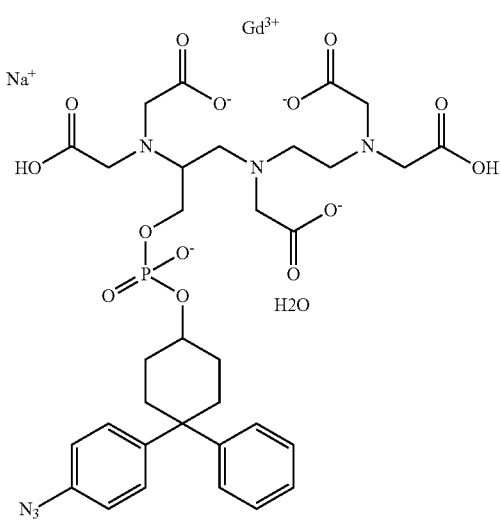

The reactive group of the gadolinium contrast agent is reactive with groups on the capture substrate. The capture substrate can be, for example, a substrate or polymer having exposed strained alkyne functional groups. The reactive receptor group can be, for example, OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

The functionalized gadolinium contrast agent spontaneously forms a covalent bond with the capture substrate. In some embodiments the functionalized gadolinium contrast agent and the capture substrate form a tri-azole ring.

An example reaction for demonstrating the sequestration reaction is shown below, with (1R,8S,9s)-Bicyclonon-4-yn-9-ylmethanol (representing a contrast agent) allowed to react with azide-fluor 488 (representing a capture substrate).

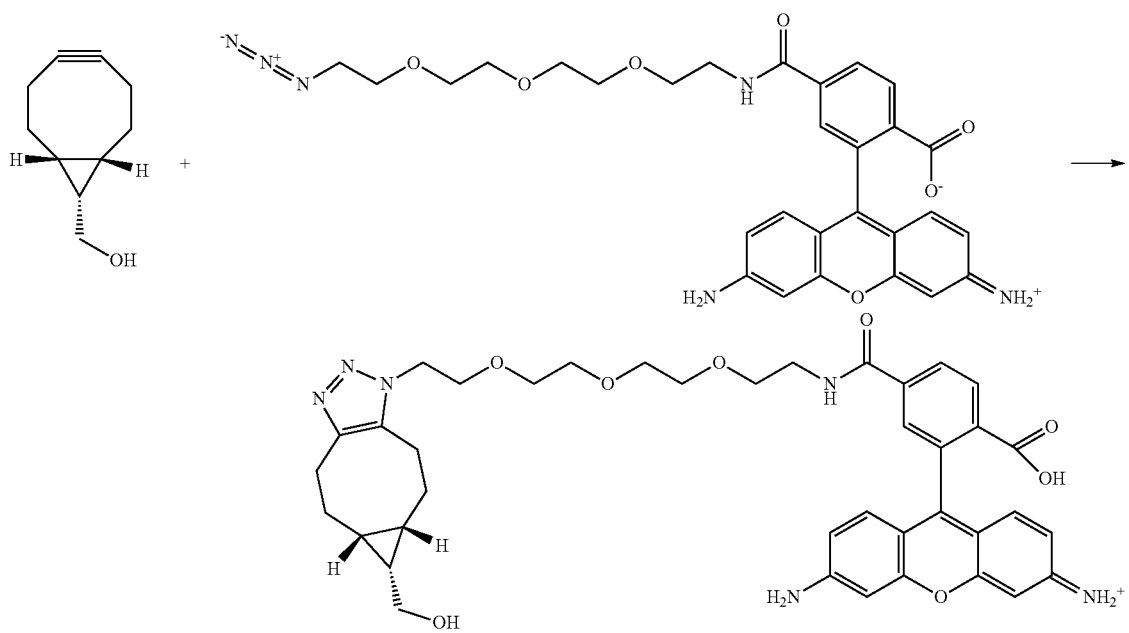

Under in vitro conditions the reaction proceeded very rapidly and was complete before a nuclear magnetic resonance (NMR) tube containing the reaction constituents could be inserted into the probe.

The capture substrate is, for example, porous so that blood and gadolinium contrast agent flows through the substrate so as to remove the gadolinium contrast agent. Alternatively, the substrate can be relatively smooth, allowing blood and gadolinium contrast agent to flow along the surface of the substrate until the contrast agent is captured. Suitable capture substrates include, for example, polyvinyl alcohol (PVA) to which the capture molecule (such as a moiety containing a strained alkyne) has been secured. The modified gadolinium contrast agent is brought in contact with the substrate after the MRI procedure, such as by insertion into a blood vessel or retained in a chamber outside of the body but through which blood is passed. An example location of the capture substrate is in the renal artery upstream of a patient's kidney.

The gadolinium contrast agents described herein can be used as part of a method of removing gadolinium contrast agents from a patient, the method comprising providing a gadolinium contrast agent having a reactive group; providing a removable capture substrate; administering the gadolinium contrast agent to the patient; conducting a magnetic resonance imaging procedure; and sequestering the gadolinium contrast agent on the removable capture substrate.

The gadolinium contrast agent can be captured and removed as part of a system comprising a gadolinium cation secured (such as by bonding, such as by ionic forces) to a ligand comprising a reactive group capable of bonding to a capture substrate; and a capture substrate. The gadolinium cation secured to a ligand can include an azide reactive group; and the capture substrate can include a polymer containing a strained alkyne; the strained alkyne selected from the group OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

Figure 5:
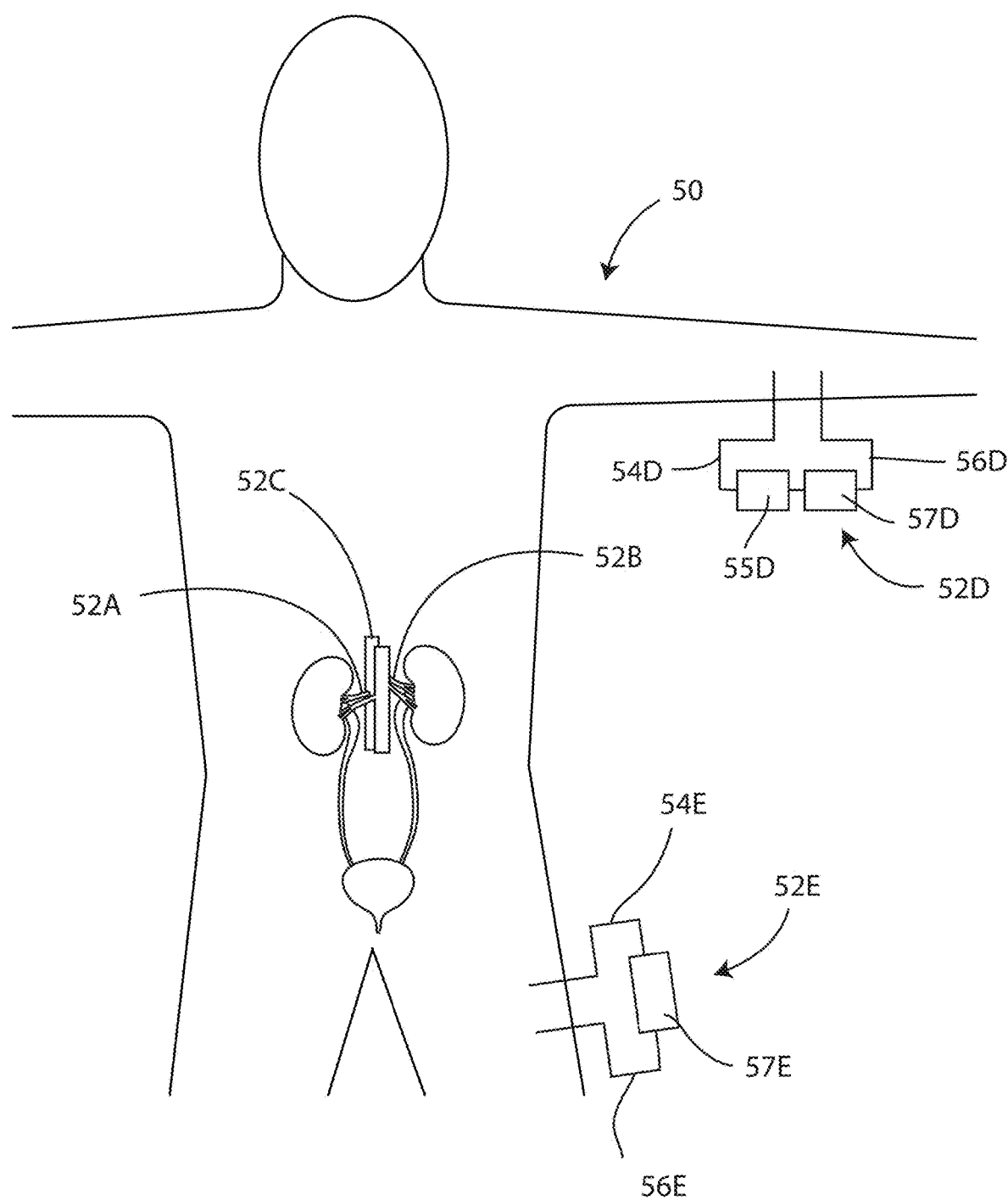
FIG. 5 is a schematic diagram showing example locations of gadolinium contrast agent scavenger positioned inside and outside a patient's body.

Now, in reference to FIG. 5, a schematic diagram of a patient 50 shows example locations 52A, 52B, 52C, 52D and 52E for a gadolinium contrast agent scavenger. Patient 50 is shown as a human outline, but examples are not so limited and may include any mammalian. FIG. 5 is simplified and not drawn to scale, showing body organs and scavenger systems schematically only. The locations 52A to 52E are shown for illustrative purposes, indicating how the location of the contrast agent scavenger can be varied. Locations 52A, 52B and 52C are all internal locations in which the contrast scavenger agent is inserted into a blood vessel, typically a blood vessel upstream of one or both kidneys. For example, locations 52A and 52B show locations at the right and left renal arteries, respectively, while location 52C is in the inferior vena cava. In such implementations the gadolinium contrast agent scavenger can be applied in the form of a textile, membrane, foam, gel, web or other substance inserted into the blood vessel and then removed after the medical procedure is completed and adequate contrast agent has been scavenged.

FIG. 5 also shows schematic representations of two external locations 52D and 52E for removing gadolinium contrast agents from the patient 50. Location 52D is shown on a peripheral body location, with an intravenous catheter 54D leading to an optional pump 55D that flows into a sequestering element 57D and then back into the patient 50 by way of intravenous catheter 56D. The sequestering element 57D contains a textile, membrane, foam, gel, web or other substance with exposed sequestering agent for binding the gadolinium contrast agent. Alternative location 52E for removing gadolinium contrast agents includes intravenous catheter 54E leading to sequestering element 57E and then flow out through return catheter 56E. Location 52E is depicted without an auxiliary pump, although generally some sort of mechanism is used to apply adequate pressure to return the blood to the patient.

External positioning of the contrast agent scavenger at location 52D and 52E are less invasive than inserting the contrast agent scavenger into locations 52A, 52B or 52C, but is also typically slower to remove the contrast agent and allows initial exposure of the kidneys of higher levels of contrast agent.

Figure 6:
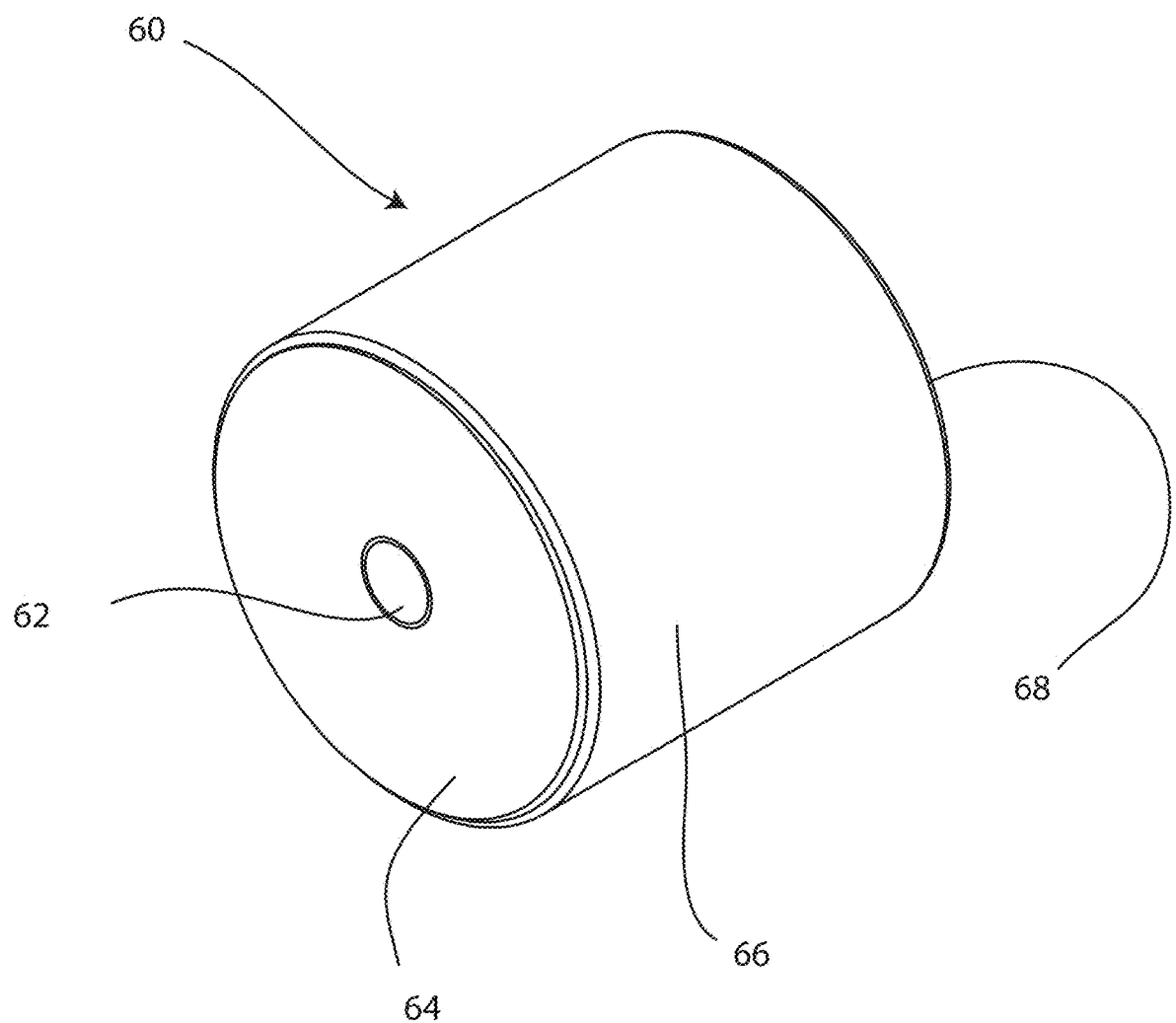
FIG. 6 is a perspective view of an article containing a gadolinium contrast agent scavenger configured for the flow of blood through the article to retain the gadolinium contrast agent.

FIG. 6 is a perspective view of gadolinium capture element 60 containing a gadolinium contrast agent scavenger configured for the flow of blood through the element to retain the gadolinium contrast agent such as elements 57D and 57E of FIG. 5. The capture element 60 includes a housing 66, along with an inlet 62 on a first end 64 of the housing 66 for receiving blood containing gadolinium contrast agent, plus an outlet (not shown) opposite the inlet 62 on the second end 68 of the housing, through which the blood exits the housing 66. Within the housing 66 is capture media. The capture media contains capture substrate as described herein, such as a capture substrate having exposed strained alkynes available for reacting with functionalized gadolinium contrast agent, such as gadolinium functionalized with an azide group.

It should also be noted that, as used in this specification and the appended claims, the phrase "configured" describes a system, apparatus, or other structure that is constructed to perform a particular task or adopt particular characteristics. The phrase "configured" can be used interchangeably with other similar phrases such as "arranged", "arranged and configured", "programmed" "constructed and arranged", "constructed", "manufactured and arranged", and the like.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A method of removing gadolinium contrast agents from a patient, the method comprising:
   providing a gadolinium contrast agent comprising a ligand containing a reactive group capable of bonding to a biorthogonal capture molecule on a removable capture substrate;
   providing a removable capture substrate comprising a polymeric film, gel, web, fabric, foam, mesh or other material to which capture molecules have been secured, the capture substrate containing capture molecules that spontaneously biorthogonally bond to the reactive group of the gadolinium contrast agent;
   administering the gadolinium contrast agent to a patient;
   conducting a magnetic resonance imaging procedure;
   sequestering the gadolinium contrast agent on the removable capture substrate; and
   removing the gadolinium contrast agent sequestered to the capture substrate from the patient without passing the capture substrate through the patient's kidney.

2. The method of claim 1, wherein the removable capture substrate is positioned in a blood vessel upstream of the kidney of the patient during sequestration of the gadolinium contrast agent.

3. The method of claim 1, wherein the gadolinium contrast agent comprises a plurality of amine groups.

4. The method of claim 1, wherein the gadolinium contrast agent comprises an azide group.

5. The method of claim 1, wherein the gadolinium contrast agent comprises an azide, alkyne, tetrazine, fluorosydnones, or combinations thereof.

6. The method of claim 1, wherein the capture substrate comprises group OCT (cyclooctyne), DIMAC (dimethoxyazacyclooctyne), DIFO (difluorinated cyclooctynes), BCN (bicyclononyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

* * * * *